United States Patent [19]
Billson et al.

[11] Patent Number: 5,770,589
[45] Date of Patent: Jun. 23, 1998

[54] TREATMENT OF MACULAR DEGENERATION

[75] Inventors: Francis Alfred Billson; Philip Leslie Penfold, both of New South Wales, Australia

[73] Assignee: The University of Sydney, New South Wales, Australia

[21] Appl. No.: 586,750
[22] PCT Filed: Jul. 27, 1994
[86] PCT No.: PCT/AU94/00424
  § 371 Date: Sep. 27, 1996
  § 102(e) Date: Sep. 27, 1996
[87] PCT Pub. No.: WO95/03807
  PCT Pub. Date: Feb. 9, 1995

[30] Foreign Application Priority Data

Jul. 27, 1993 [AU] Australia .................. PM0182

[51] Int. Cl.$^6$ .................................................. A61K 31/58
[52] U.S. Cl. .................................................. 514/174
[58] Field of Search .................................................. 514/174

[56] References Cited

PUBLICATIONS

Chandler et al, Chemical Abstracts, vol. 107, abstract No. 229394, 1987.

Primary Examiner—William R. A. Jarvis
Attorney, Agent, or Firm—Jenkins & Wilson, P.A.

[57] ABSTRACT

In the treatment of age-related macular degeneration, a method for treating an inflammatory response in the macula of the eye by use of a depot injection of a suitable anti-inflammatory agent into the vitreous humour is described. Triamcinolone acetomide (T) is employed which is in crystalline form and is sparingly soluble in the vitreous of the eye, and which does not leave any vision impairing residue in the eye.

15 Claims, 1 Drawing Sheet

TREATMENT OF MACULAR DEGENERATION

This application claims priority under 35 U.S.C. 371 to PCT/AU94/00424, filed Jul. 27, 1994.

TECHNICAL FIELD

The present invention relates to the treatment of inflammatory response in the macula of the eye[1,2,3,4,5,6] by use of a depot injection into the vitreous humour of a suitable anti-inflammatory agent. In particular it relates to the treatment of age-related macular degeneration and more particularly relates to the treatment of the end stage of this condition with anti-inflammatory steroids. This end stage previously has been presumed to be untreatable.

BACKGROUND ART

The major cause of registrable blindness in developed countries is due to the condition known as age-related macular degeneration[7]. In this condition, the macula which is a minute area in the centre of the retina is damaged. The macula occupies a total area of less than 1 mm$^2$. This area is especially adapted for acute and detailed vision. In the central portion of the macula, known as the fovea (which is 0.4 mm in diameter) the blood vessels, and other cells are displaced to the side, allowing light to fall onto the photosensitive layer. This is in contrast to other parts of the retina where light has to pass through several layers of tissue before arriving at the photosensitive layer.

The condition itself is conveniently divided into three stages. It may present as early stage macular degeneration. At least 20% of patients develop an active neurovascular form.

One end stage of this condition is known as atrophic macular degeneration (AMD) while a second end stage is known as neovascular macular degeneration (NMD), which is caused when new blood vessels begin to grow under the retina, particularly the macula.

AMD is not treatable, whereas NMD in some cases may be relieved by laser treatment. However, a complication of laser treatment is actual loss of vision. In addition, laser treatment, where applicable, is not always a permanent cure since the blood vessels may begin to grow again.

The problem of macular degeneration is immense. It has been estimated that 25% of people 70 and over in the developed world will have the mild form of the condition while 1 in 10 have severe symptoms and 1 in 100 progress to complete blindness.

The present inventors have recently demonstrated that intravitreal injection of an anti-inflammatory steroid in depot form substantially arrests and/or reverses AMD and NMD.

It has been shown[8,9] that intravitreal administration of anti-inflammatory steroids inhibits vascular proliferation in the eye. The inventors have shown[1,2,3,4,5] in human patients that AMD is promoted by choroidally derived inflammatory cells. The inventors recently described resident immunocompetent cells[5] in the neural retina which would be subject to the influence of intravitreal anti-inflammatory steroids.

DISCLOSURE OF THE INVENTION

According to a first form of this invention there is provided a method for the treatment or prophylaxis of macular degeneration in a patient requiring said treatment or prophylaxis, comprising administering by intravitreal injection to said patient an effective amount in depot form of an anti-inflammatory steroid which is preferably sparingly soluble in the vitreous, Preferred steroids include 11-substituted 16α,17α-substituted methylenedioxy steroids of the formula

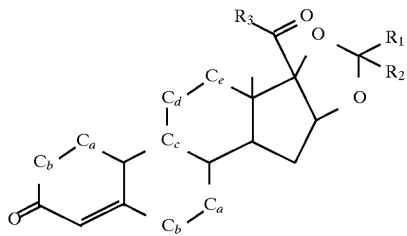

wherein

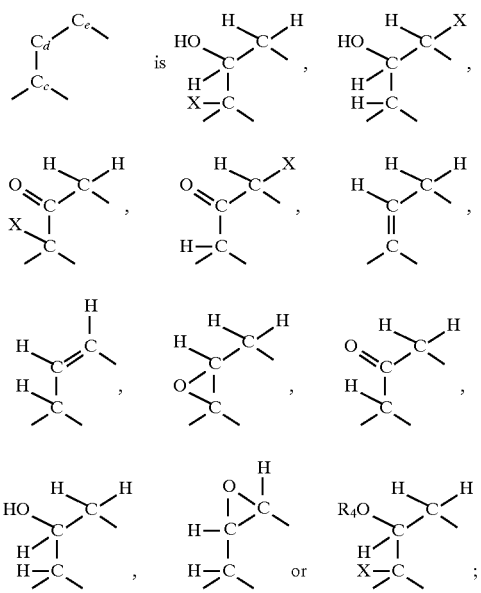

$R_1$ and $R_2$ are hydrogen or alkyl;

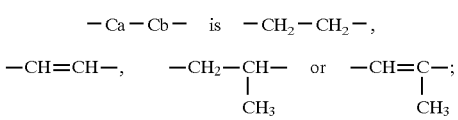

$R_3$ is methyl, hydroxymethyl or alkylcarbonyloxymethyl, methylaminoalkylenecarbonyloxymethyl, or phenylamino alkylenecarbonyloxymethyl; $R_4$ is alkanoyl; and X is halogen.

More preferred are compounds of the formula

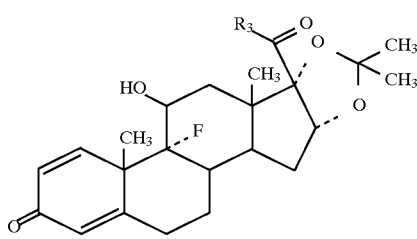

wherein $R_3$ is hydroxymethyl, phenylcarbonylaminoisopropylcarbonyloxymethyl, or 2,2-dimethylpropylcarbonyloxymethyl.

The preferred steroid is crystalline 9-fluoro-11,21-dihydroxy-16,17-[1-methylethylidinebis(oxy)]pregna-1,4-diene-3,20-dione:

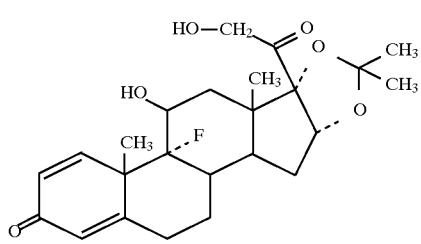

This compound, also known by its generic name as triamcinolone acetonide is suitably prepared by known methods[10,11,12,13].

The steroids are preferably crystalline and are administered in distilled water with a minimum of carriers or adjuvants. However, a depot pharmaceutical composition comprising an effective amount of said anti-inflammatory steroid together with a pharmaceutically and opthalmologically acceptable carrier, diluent and/or excipient may be used.

When triamcinolone acetonide is used, such a preparation may be made up by using Kenacort-A40 (registered trade mark) (Squibb) as the anti-inflammatory steroid. Suitable pharmaceutically acceptable salts of this compound may be used. For example, the acetate of triamcinolone acetonide may be used.

As the steroids suitable for use in this invention are sparingly soluble in the vitreous, crystalline forms are suitable for administration. The steroids may be formulated with carriers, diluents and/or excipients which are compatible with the vitreous and which do not leave any vision impairing residue in the eye.

The composition of the present invention is administered by intravitreal injection by methods known in the art. For example, the eye is washed with a sterilising agent such as Betadine and the steroid is injected in distilled water with a fine gauge (eg. 27 gauge) needle at a position in the eye such that the steroid crystals will settle to the posterior pole towards the ventral surface. It may also be necessary to prepare the eye for injection by application of positive pressure prior to injection. In some cases, paracentesis may be necessary.

The steroid should be as concentrated as feasible to minimise the volume to be injected. The dosage of steroid may be between about 1 mg and about 8 mg. Typically, 4 mg of steroid is deposited intravitreally and thus it is necessary to inject 0.1 mL of Kenacort-A40 solution. This dosage range is applicable to each of the three following stages of macular degeneration, namely: early onset macular degeneration, atrophic macular degeneration (AMD) and neovascular macular degeneration (NMD).

The frequency of method of treatment of this invention is not more than 3 monthly. In many cases, a single administration per annum may be sufficient.

The compositions of this invention may also be presented as a unit dose in a syringe ready for administration.

The method of the present invention may be practised alone or in conjunction with other therapy. Where laser treatment of the retina is indicated, steroid may be injected before or after the laser treatment. Other substances, for example antibiotics and anti-angiogenesis agents for example thalidomide, may be injected with the steroid.

In more than 50% of cases where AMD occurs in one eye, it will occur in the other eye within one year. Prophylactic administration of steroid into an unaffected eye may be useful in such cases.

BEST MODES AND OTHER MODES FOR CARRYING OUT THE INVENTION

Figure 1:
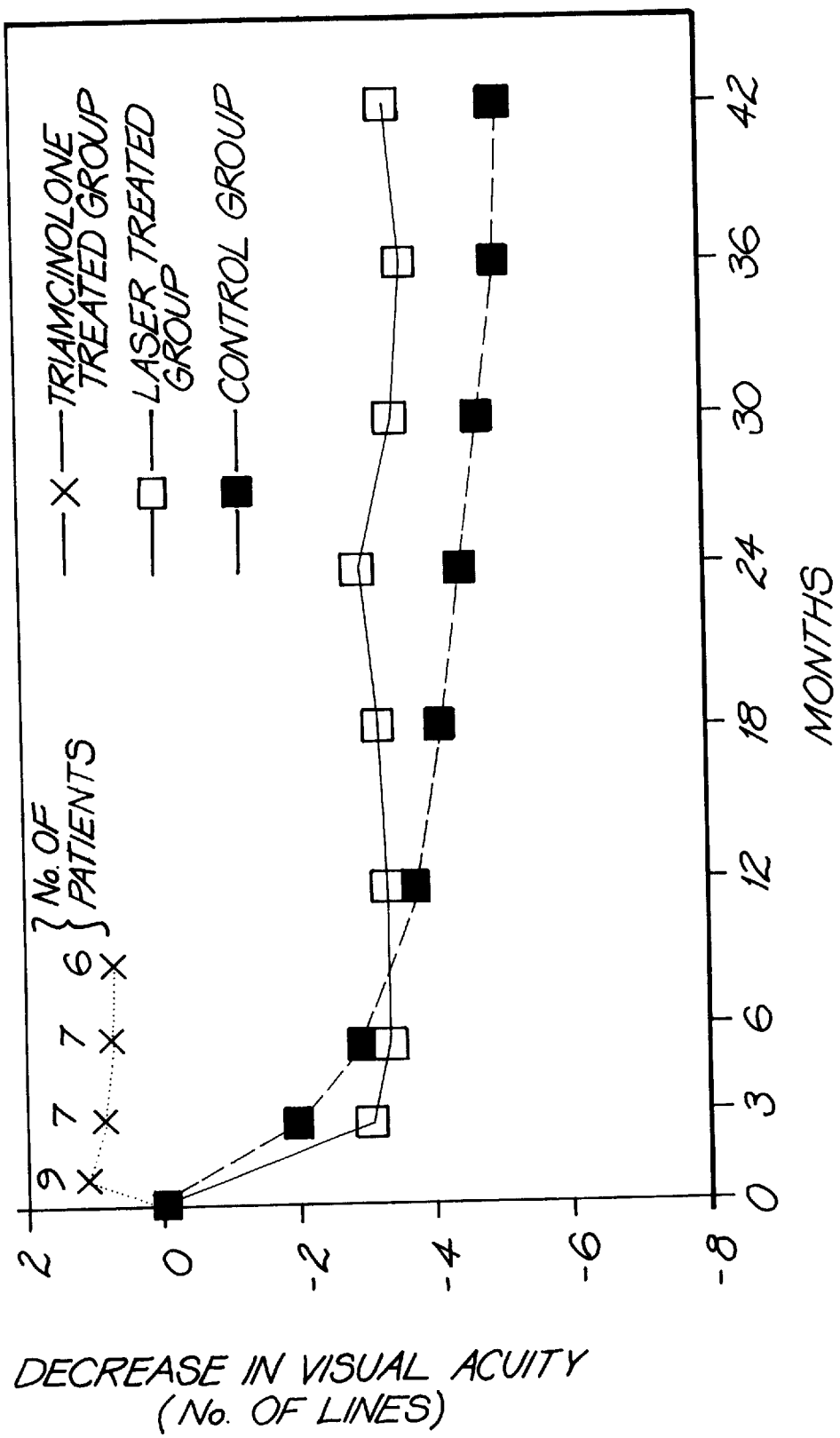
FIG. 1 is a comparison between change in visual acuity in three groups of patients.

An effective amount of triamcinolone acetonide to arrest and/or reverse macular degeneration is administered by intravitreal injection when such a procedure is indicated.

The present invention will now be described with reference to the following examples which should not be construed as limiting on the scope thereof.

EXAMPLE 1

Kenacort-A40 (Squibb) (40 mg/mL) as supplied is prepared for administration of 0.1 mL.

EXAMPLE 2

Six patients were injected with 0.1 mL Kenacort-A40. The patients were monitored weekly by direct observation including colour vision, electrophysiological responses of the retina and dynamic studies of the retinal circulation using fluorescein angiography.

EXAMPLE 3

The influence of intravitreal triamcinolone on microglial distributions in AMD: a case study The source of the signals which initially provoke choroidal neovascularisation has not been defined, although immune mediation of neovascularisation by both choroidally derived leucocytes and retinal microglia remain significant possibilities. As part of a pilot study, one patient with subfoveal choriodal new vessels received intravitreal triamcinolone in her left eye. Angiography showed that exudation decreased and vision improved. Unfortunately, the patient died within 6 weeks of the administration as a result of cardiovascular failure, but donated her eyes for histopathological examination. The immunohistopathological findings of this unique case study are summarised below.

Methods: Eyes were fixed in 2% paraformaldehyde for 24 hours at 4° C. The delay between death and fixation of both eyes was 25 hours. Following fixation, the neural retina was separated from RPE (ie retinal pigment epithelium)/choroid portion which was postflxed and examined histopathologically in semithin sections. Primary monoclonal antibodies (MHC class II & CD45) were applied to retinal wholemounts and detected using silver-toned immunogold.

The distributions and phenotypic characteristics of microglia in normal age-matched adult retinae, the treated and untreated retinae were compared.

Results: Both the treated and the untreated RPE/choroidal specimens showed similar early disciform lesions which were not obviously altered as a result of the steroid administration. Microglia were morphologically hypertrophic in the untreated retina while the number of microglia was not significantly increased, consistent with our earlier findings. However microglial morphology was less ramified and cell numbers were significantly less in the treated retina.

Conclusions: Comparison of microglial numbers labelled with MHC class II and CD45 antibodies indicated that in addition to reduced cell numbers, triamcinolone administration effected reduced expression of MHC class II by microglia, but not vascular elements.

EXAMPLE 4

Comparison between change in visual acuity In triamcinolone treatment and laser treatment FIG. 1 graphically illustrates a comparison between the change in visual acuity in a group of patients treated with triamcinolone, and a previous study involving a group of patients treated with laser therapy and a group of patients in which no treatment was given (control group). The triamcinolone group was studied for 10 months. The two previously reported groups were studied for a period of 42 months.

The table on the following page sets out the results for the triamcinolone group.

It can be seen from the graph in FIG. 1 that there was in fact an initial increase in visual acuity in the triamcinolone group. The group treated with laser therapy suffered a decrease of 3 lines of visual acuity within 3 months. This then remained stable for a period of up to 42 months. The control group experienced less of an initial, decrease falling to 2 lines within 3 months. However, the control group steadily decreased over the period of study, reaching a decrease of 5 lines of visual acuity by 42 months.

TABLE

| | | | Visual Acuity | | | | | | |
|---|---|---|---|---|---|---|---|---|---|
| Patient No | Age/Sex: | Eye: | 0/12 | 1/12 | 3/12 | 6/12 | 10/12 | Disorder (Treated Eye Only) | Drusen |
| 1. | 80/F | Left | 1 | p5 | p5 | p5 | p5 | mCNV + occCNVs + HAEM + hEx + Oed | No |
| 2. | 82/M | Left | 1 | 0 | 0 | 0 | 0 | lCNV + fib + mHAEM + EBF + Oeb | Few s |
| 3. | 80/F | Right | 9 | p2 | m2 | m2 | m6 | sCNV + EBF + Pigdist + Oed | No |
| 4. | 78/F | Right | 10 | p2 | 0 | m0.5 | p3 | sCNV + EBF + Pigdist + Oed | Few h |
| 5. | 84/M | Right | 3 | p1 | p3 | p4 | p4 | mCNV + occCNV + sHAEM + EBF + hEx | No |
| 6. | 78/F | Left | 8.5 | p1 | p0.5 | m1.5 | m1.5 | mCNV + Pigdist + EBF + Oed | No |
| 7. | 90/F | Left | 0.5 | 0 | 0 | p0.5 | N | mCNV + EBF + sHAEM + hEx + Oed | No |
| 8. | 76/F | Left | 8 | m1 | N | N | N | 2(s + m)CNV + Haem | h + c + s + a |
| 9. | 80/F | Left | 7 | 0 | N | N | N | mCNV + fibr + serDet | Many h |
| Change | | | basis | p.1.1 | p0.93 | p0.78 | p0.75 | | |

Lineage of the visual acuities
1 = 1/60
2 = 2/60
3 = 3/60
4 = 4/60
5 = 5/60
6 = 6/60
7 = 6/36
8 = 6/24
9 = 6/18
10 = 6/12
11 = 6/9
12 = 6/7.5
13 = 6/6
14 = 6/5
15 = 6/4
s = small (<1 DA), m = medium (1–2 DA)
l = large (>2 DA) occ = occult,
fib = fibrosis, serDet = serous detachment
hEx = hard exudates, EBF = elevated blocked fluorescence
Pigdist = pigment disturbance
h = hard
s = soft
c = calcified
a = atrophic

INDUSTRIAL APPLICABILITY

It should be clear that the methods of treatment of this invention will find wide use in the medical field.

The foregoing describes only some embodiments of the present invention and modifications obvious to those skilled in the art can be made thereto without departing from the scope of the invention.

REFERENCES

1 Penfold P. L. et al., "Senile macular degeneration: The involvement of Immunocompetent cells" Graefe's Arch Clin Exp Ophthalmol (1985) 223:69–76.

2 Penfold P. L. et al., "Senile Macular Degeneration The Involvement of Giant Cells in Atrophy of the Retinal Pigment Epithelium" Invest Ophthalmol Vis Sci (1986) 27:364–371.

3 Penfold P. L. et al., "Age-related macular degeneration: ultrastructural studies of the relationship of leucocytes to angiogenesis" Graefe's Arch Clin Exp Ophthalmol (1987) 225:70–76.

4 Penfold P. L. et al., "Autoantibodies to retinal astrocytes associated with age-related macular degeneration" Graefe's Arch Clin Exp Ophthalmol (1990) 228:270–274.

5 Penfold P. L. et al., "Antibodies to human leucocyte antigens indicate subpopulations of microglia in human retina" Visual Neuroscience (1991), 7, 383–388.

6 Dayton L. "Treatment for blindness challenges eye orthodoxy" New Scientist 21 March 1992.

7 Gehrs K. M. et al. "Transmission Electron Microscopic Study of a Subretinal Choroidal Neovascular Membrane due to Age-Related Macular Degeneration" Arch Ophthalmol (1992) 110, 833.

8 Ishibashi T. et al. "Effects of Intravitreal Administration of Steroids on Experimental Subretinal Neovascularization in the Subhuman Primate" Arch Ophthalmol (1985) 103, 708.

9 Antoszyk A. N. et al. "The effects of intravitreal triamcinolone acetonide on experimental pre-retinal neovascularization" Graefe's Arch Clin Exp Ophthalmol (1993) 231:34–40.

10 Fried et al., J. Am. Chem. Soc. 80, 2338 (1958).

11 Bernstein et al., Ibid. 81, 1689 (1959).
12 U.S. Pat. No. 2,990,401.
13 U.S. Pat. No. 3,035,050.

We claim:

1. A method for the treatment of macular degeneration in a patient requiring said treatment, comprising administering by intravitreal injection to said patient an effective amount of an anti-inflammatory steroid.

2. The method according to claim 1, wherein the steroid is crystalline.

3. The method according to claim 1, wherein the steroid is an 11-substituted 16α, 17α-substituted methylenedioxy steroid of the formula

[structural formula]

wherein

[structural formulas for $C_d$—$C_e$—$C_c$ group]

$R_1$ and $R_2$ are hydrogen or alkyl;

$-C_a-C_b-$ is $-CH_2-CH_2-$, $-CH=CH-$,  $-CH_2-CH-$  or  $-CH=C-$;
                  |                    |
                  $CH_3$               $CH_3$ $R_3$ is methyl, hydroxymethyl or alkylcarbonyloxymethyl, methylaminoalkylenecarbonyloxymethyl, or phenylaminoalkylenecarbonyloxymethyl; $R_4$ is alkanoyl; and X is halogen.

4. The method according to claim 3, wherein the steroid is:

[structural formula]

wherein $R_3$ is hydroxymethyl, phenylcarbonylaminoisopropylcarbonyloxymethyl, or 2,2-dimethylpropylcarbonyloxymethyl.

5. The method according to claim 4, wherein the steroid is 9-fluoro-11,21-dihydroxy-16,17-[1-methylethylidinebis (oxy)]pregna-1,4-diene-3,20-dione:

[structural formula]

6. The method according to claim 1 wherein the dosage of steroid is between about 1 and about 8 mg.

7. The method according to claim 6 wherein the dosage is about 4 mg.

8. The method according to claim 1 wherein the macular degeneration is early onset macular degeneration, atrophic macular degeneration or neovascular macular degeneration.

9. The method according to claim 1, further comprising an additional active ingredient.

10. The method according to claim 9, wherein the additional active ingredient is an anti-angiogenesis agent.

11. The method according to claim 10, wherein the anti-angiogenesis agent is thalidomide.

12. The method according to claim 9, wherein the additional active ingredient is an antibiotic.

13. The method according to claim 1 wherein the method is practised in conjunction with another therapy.

14. The method according to claim 13, wherein the other therapy is laser treatment of the retina and the anti-inflammatory steroid is injected before or after laser treatment.

15. A method for the prophylaxis of macular degeneration in a patient in need thereof comprising administering to said patient by intravitreal injection an effective amount of an anti-inflammatory steroid.

* * * * *